(12) United States Patent
Upadhyay et al.

(10) Patent No.: US 7,674,824 B2
(45) Date of Patent: Mar. 9, 2010

(54) STABLE OXALIPLATIN FORMULATION

(75) Inventors: Satish Chandra Upadhyay, Sahibabad Ghaziabad (IN); Manoj Kumar Pananchukunnath, Sahibabad Ghaziabad (IN); Ajeet Kumar Singh, Sahibabad Ghaziabad (IN); Deepti Jain, Sahibabad Ghaziabad (IN); Deepak Judgelal Parshotamdas, Sahibabad Ghaziabad (IN); Rama Mukharjee, Sahibabad Ghaziabad (IN); Anand C Burman, Sahibabad Ghaziabad (IN)

(73) Assignee: Fresenius Kabi Oncology Limited, New Delhi (IN)

( * ) Notice: Subject to any disclaimer, the term of this patent is extended or adjusted under 35 U.S.C. 154(b) by 401 days.

(21) Appl. No.: 11/515,553

(22) Filed: Sep. 5, 2006

(65) Prior Publication Data

US 2007/0054957 A1 Mar. 8, 2007

(51) Int. Cl.
*A61K 31/282* (2006.01)
(52) U.S. Cl. ..................... 514/492; 514/574
(58) Field of Classification Search ........... 514/492
See application file for complete search history.

(56) References Cited

U.S. PATENT DOCUMENTS

| | | | |
|---|---|---|---|
| 4,169,846 A | 10/1979 | Kidani et al. | |
| 5,716,988 A | 2/1998 | Ibrahim et al. | |
| 6,306,902 B1 * | 10/2001 | Anderson et al. | 514/492 |
| 6,476,068 B1 * | 11/2002 | Lauria et al. | 514/492 |
| 6,601,721 B2 * | 8/2003 | Jansen et al. | 215/249 |
| 2003/0109515 A1 | 6/2003 | Lauria et al. | |
| 2004/0186172 A1 * | 9/2004 | Ibrahim | 514/492 |
| 2005/0090544 A1 | 4/2005 | Whittaker et al. | |

FOREIGN PATENT DOCUMENTS

| | | |
|---|---|---|
| EP | 1 466 599 A1 | 10/2004 |
| EP | 1 466 600 A1 | 10/2004 |
| WO | 01/15691 | 3/2001 |

OTHER PUBLICATIONS www.westpharma.com, 2004, 2 pages.*
Alberts et al. (Annals of oncology (2002), 13(4) pp. 553-557.*

* cited by examiner

*Primary Examiner*—Michael G Hartley
*Assistant Examiner*—Shirley V Gembeh
(74) *Attorney, Agent, or Firm*—Merchant & Gould P.C.

(57) ABSTRACT

A storage stable pharmaceutical composition comprising a solution of Oxaliplatin in water and a catalytic amount of a carbohydrate. A process for forming such pharmaceutical composition comprising dissolving a known amount of Oxaliplatin in water; adding an amount of carbohydrate in the range of 0.0010% to 0.05% w/v with respect to such solution; agitating the mixture to get clear solution; filtering it through a filter membrane under aseptic conditions; and filling the solution resulting into glass vials sealed with elastomeric stoppers and aluminium flip-off seals.

12 Claims, No Drawings

STABLE OXALIPLATIN FORMULATION

FIELD OF THE INVENTION

The present invention relates to a parenterally administrable, stabilized pharmaceutical composition of oxaliplatin and a process for preparation thereof.

BACKGROUND OF THE INVENTION

Platinum (II) complexes have found wide acceptance for treatment of variety of tumors, especially Lung cancer, Lymphoma, Ovarian cancer, Testicular cancer, Bladder cancer, Urothelial cancer and Head/neck cancer in both humans and animals. Of these platinum analogues, oxaliplatin (U.S. Pat. No. 4,169,846), also known as L-OHP, a third generation platinum complex containing diamino cyclohexane carrier ligand, is approved for the treatment of advanced carcinoma of the colon or rectum in combination with infusional 5-FU/LV.

Currently, the marketed formulations of oxaliplatin are available as a lyophilized or freeze dried powder, which just prior to administration are reconstituted using an aqueous solvent, preferably water for injection, and administration of the solution thus obtained subsequent to dilution with dextrose solutions.

However, the lyophilized oxaliplatin formulation is associated with several disadvantages such as:
  a) Double handling: To administer a lyophilized preparation, double handling of the drug is required. The lyophilized cake has to be first reconstituted and then administered;
  b) Dissolution time of the cake: In some cases, the complete dissolution of the powder may require prolonged shaking because of solubilisation problems;
  c) Health Hazard: Improper reconstitution of a lyophilized powder sometimes result in the formation of air-borne droplets ("blow-back"), which, in the case of a potent antitumor agent such as platinum complexes may be a health hazard to the personnel making up the solution for injection;
  d) Improper dose: There is always a problem in reconstituting a lyophilized powder in that an inappropriate quantity of diluents may be used because of a different vial size. This could result in an improper dose being administered to a patient; and
  e) Cost of manufacture: The manufacture of a lyophilized formulation is quite costly, since it not only requires capital investment for installation of a lyophilizer, but also its maintenance.

Generally, the stability of the reconstituted solution is not a major issue, since such solutions need to be administered immediately or within a prescribed time, generally not exceeding 8 hrs. However, Oxaliplatin is an exception since, following reconstitutions, oxaliplatin is prone to instability, particularly in solutions containing certain nucleophilic agents. For example, some reconstitution solutions containing chloride ions, such as 0.9% sodium chloride solutions, also known as normal saline solutions, which is very commonly used in hospitals, if used for such a reconstitution of oxaliplatin lyophilized powder, has the serious consequence of rapidly decomposing the oxaliplatin metal complex, forming a precipitate (dichloro-diaminocyclohexane-platinum complex).

As a consequence of the abovementioned limitations, several ready-to-use, aqueous pharmaceutical compositions of oxaliplatin have been proposed:

a) In U.S. Pat. No. 5,716,988, Ibrahim et al disclose a pharmaceutically stable oxaliplatin preparation for parenteral administration comprising an aqueous solution of oxaliplatin, in a concentration of 1 to 5 mg/ml, and with a pH in the range of 4.5 to 6. The specification states that this preparation is free of any other components and should, in principle, not contain more than about 2% of impurities. However, subsequently, U.S. Pat. No. 6,306,902 and U.S. Pat. No. 6,476,068 report that the simple aqueous solutions of oxaliplatin prepared according the teachings of this particular patent are insufficiently stable.

b) In U.S. Pat. No. 6,306,902, Anderson et al disclose a stable oxaliplatin solution formulation comprising therapeutically effective amount of oxaliplatin, an effective stabilizing amount of a buffering agent and a pharmaceutically acceptable carrier wherein the buffering agent is oxalic acid or an alkali metal salt thereof.

c) In U.S. Pat. No. 6,476,068, Lauria et al disclose a stable oxaliplatin solution formulation comprising oxaliplatin, and effective stabilizing amount of lactic acid and/or a pharmaceutically acceptable salt of lactic acid and a pharmaceutically acceptable carrier.

d) In WO 01/15691, Ibrahim et al disclose pharmaceutically stable solutions of at least 7-mg/ml oxaliplatin containing a sufficient amount of a solvent having at least a hydroxylated derivative selected from 1,2-propane-diol, glycerol, maltitol, saccharose and inositol. The specification states that these are the only suitable agents and the limited choice of hydroxylated derivatives to use has been done following a very large number of experiments and after consideration of several options.

e) In U.S. Ser. No. 03/0,109,515, Lauria et al disclose a stable oxaliplatin solution formulation comprising oxaliplatin, and effective stabilizing amount of malonic acid and/or a pharmaceutically acceptable salt of malonic acid and a pharmaceutically acceptable carrier.

f) In EP 1466599, Schridde et al disclose a infusion-concentrate containing oxaliplatin and a physiologically compatible carbohydrate as solubility enhancer.
The specification states that, with higher concentrations of carbohydrates, the formation of the degradation or the reaction products of oxaliplatin caused by the presence of hydroxide anions is drastically reduced or suppressed. Further, since these solutions containing carbohydrates are suitable for solublising the oxaliplatin, the concentration of carbohydrates, preferably glucose, should be at least 50 mg/ml.

g) In EP 1466600, Schridde et al disclose an oxaliplatin solution, which preferably in addition contain sulfuric acid, phosphoric acid, ethane sulfonic acid, or para-toluosofonic acid.

h) In U.S. Ser. No. 05/0,090,544, Whittaker et al disclose a pharmaceutical liquid formulation of oxaliplatin for parenteral administration comprising oxaliplatin, water and an additive selected from the group consisting of tartaric acid, a salt of tartaric acid, a pharmaceutically acceptable derivative of tartaric acid and mixtures thereof.

From the abovementioned disclosures, it would be apparent that most, if not all the methods for stabilization of oxaliplatin solutions involve utilization of buffering agents to adjust the pH of the formulation and to maintain the formulation within a desired pH range. As mentioned above, several dicarboxylic acids such as oxalic acid, lactic acid, malonic acid, tartaric acid, several monocarboxylic acid such as sulfuric acid, phosphoric acid, ethane sulfonic acid, or paratoluenesulfonic acid and their pharmaceutically acceptable salts have been proposed as a buffering and stabilizing agent for oxaliplatin. However, most of these auxiliary substances have several disadvantages, which limits their use in pharmaceutical products. For example utilization of oxalic acid or its salt, which because of Le Chatelier's principle reduces the formation of oxalate ion, generated by hydrolysis of oxaliplatin in aqueous solution, has notable nephrotoxicity. Further, in the intravenous therapy, higher concentrations of oxaliplatin or oxalate ion pose the risk of local and systemic side effects such as local pain, aggregation of thrombocytes, thrombosis, kidney stones etc. making, in general, the addition of oxalate ions in injection non-desirable, a plausible reason why oxalic acid or for that matter malonic acid utilized as additives in U.S. Pat. No. 6,306,902 and U.S. Ser. No. 03/0,109,515 are not approved by the USFDA for inclusion into a parenteral composition.

Moreover, for selection of an appropriate auxiliary substance to achieve stabilization, there is neither any general guideline nor can an inference be drawn from the teachings of the abovementioned specification. For e.g. U.S. Pat. No. 6,306,902 discloses that, except oxalic acid, utilization of other buffering agents such as acetate, citrate, phosphate, glycine or tris buffer does not stabilize the aqueous solution of oxaliplatin. U.S. Pat. No. 6,476,068 also supports and suggests that acetate and citrate buffers are not suitable for oxaliplatin solutions. However, exactly opposite is the teaching of EP 1,466,600, which states that phosphoric, sulfuric and other acids could be utilized for preparing a stable oxaliplatin solution.

Another approach utilized in stabilizing the oxaliplatin solution is through enhancing the solubility of oxaliplatin as disclosed in WO 01/15691, by adding 1,2-propane diol, glycerin, maltitol, saccharose, or inositol or as disclosed in EP 1,466,599 by adding a physiologically compatible carbohydrate in at least 50 mg/ml concentrations. However, all these additives have immense disadvantages when used at the specified concentrations for preparation of injectable medicinal solutions. All of these carbohydrates are most easily available sources of energy, which can lead unbalancing of metabolism, especially owing to widely spread diabetes mellitus in the therapy of oxaliplatin caused by age. Moreover, inositol and glucose are physiologically important intracellular sugars and their salts are essential components of signal transduction cascade. Inositol is also administered orally and intravenously in experimental therapy as maturing promoter in pre-mature babies. Further it also has unwanted potential of neurological side effects.

Further, it might be mentioned that other hydroxylated derivatives as disclosed in WO 01/15691 do not belong to the standard auxiliary substances with known side effects, which are used for preparing the parenteral solutions. These compounds are normally used only in pharmaceutical preparations as auxiliary substances for external or oral use and are not recommended by Health Authorities worldwide or the parenteral use.

It might be further mentioned that Health Authorities all over the world are very concerned about the level of degradation products and impurities present in a drug substance or a drug product. As a consequence, regulatory approval norms today are very stringent about the level of impurities present in a drug substance or a drug product. In view of this, it is rather intriguing how an oxaliplatin solution containing more often than not amounts of additives in such a higher percentage as suggested by the prior teachings could comply with pharmacopoeial specifications, even though such solutions may be stable.

From the foregoing, it would be apparent that there is no universal method or system for stabilization of an oxaliplatin solution, which is simple, convenient, economical and is not dependent on the vagaries of critical parameters like pH, amount and nature of additives, specially requisite mono carboxylic acid or dicarboxylic acid, or nature of hydroxylated solvents etc.

A need, therefore, exists for a pharmaceutical composition of oxaliplatin which is universal, simple, convenient, and is not dependent on the vagaries of critical parameters like pH, nature and amount of additives specially requisite monocarboxylic acid or dicarboxylic acid, nature of hydroxylated solvents etc.

The present invention is a step forward in this direction and overcomes most, if not all the limitations of the prior art methods in providing a novel and simple method for stabilization of oxaliplatin solutions.

OBJECTS OF THE INVENTION

An object of the present invention is to provide a pharmaceutical composition of oxaliplatin, which is stable on storage for pharmaceutically acceptable duration of time.

Another object of the present invention is to provide a pharmaceutical composition of oxaliplatin, which is stable and undergoes less degradation.

Yet another object of the present invention is to provide a pharmaceutical composition of oxaliplatin, which can be stabilized by use of a catalytic amount of a suitable additive.

Yet further object of the present invention is to provide a pharmaceutical composition of oxaliplatin, which can be stabilized by use of a catalytic amount of a suitable additive, which is not associated with nephrotoxicity, as well as other local systemic side effects.

Another object of the present invention is to provide a pharmaceutical composition of oxaliplatin, which can be stabilized by use of a catalytic amount of a suitable additive, which does not lead to any unbalancing of metabolism, especially diabetes mellitus.

Yet another object of the present invention is to provide a process for preparation of a stable pharmaceutical composition of oxaliplatin, which is simple, convenient and economical.

A further object of the present invention is to provide a method for treatment of a human or an animal cancerous disease, comprising administration of such stable pharmaceutical compositions of oxaliplatin, to the human or animal in need of said treatment.

SUMMARY OF THE INVENTION

Thus according to main aspect of present invention there is provided a storage stable pharmaceutical composition comprising a solution of Oxaliplatin in water and a catalytic amount of a carbohydrate.

DETAILED DESCRIPTION OF THE INVENTION

In their endeavor to find a suitable method for stabilization of a ready-to-use aqueous solution of oxaliplatin, the present inventors have found to their surprise that indeed such a solution could not only be rendered to possess a remarkably long storage life but also, exhibit a negligible drop in potency as well as significantly superior quality in terms of minimal and acceptable levels of degradation products and impurities formed during storage of the solution.

It has been found that such a ready-to-use aqueous solution of oxaliplatin possessing long storage life with a negligible drop in potency and significantly superior quality in terms of minimal and acceptable levels of degradation products and impurities formed during storage of the solution could be obtained by addition of a catalytic amount of an additive to the solution.

Further, it has been found that such a ready-to-use aqueous solution of oxaliplatin possessing long storage life with a negligible drop in potency and significantly superior quality in terms of minimal and acceptable levels of degradation products and impurities formed during storage of the solution could be obtained by addition of a catalytic amount of a carbohydrate to the solution.

The carbohydrates that could be used for stabilization of the composition are selected from those routinely utilized in pharmaceutical preparations such as glucose, lactose, dextrose, sucrose etc.

It has been found that the carbohydrates when utilized in an amount ranging from 0.0010% to 0.05% w/v of the solution of oxaliplatin are found to impart the desired storage stability to the solution. However, optimum stability with negligible drop in potency and significantly superior quality in terms of minimal and acceptable levels of degradation products and impurities formed during storage is found to be achieved when the carbohydrates are utilized in an amount ranging from 0.0010% to 0.02% w/v of the solution of oxaliplatin, more preferably in an amount ranging from 0.0010% to 0.005% w/v of the solution of oxaliplatin.

Further, utilization of the abovementioned concentration of the carbohydrate in the composition has been found to not only conserve the original/initial potency or assay of the drug substance i.e. Oxaliplatin during thermal storage but also found to lead to minimal formation of related substances or degradation products as well as other impurities, which moreover, comply with pharmacopoeial requirements.

In particular, an aqueous ready-to-use solution of oxaliplatin containing a catalytic amount of any one of the aforementioned carbohydrates in a concentration of 0.0010% to 0.02% w/v is found to be superior to those solutions wherein a "non-catalytic amount" of same carbohydrates have been employed, especially in a concentration of >0.05%, and in particular, in a concentration of 5% to 50% as taught by Schridde et al in EP 1466599. Further, it has been found that an aqueous ready-to-use solution of oxaliplatin containing catalytic amount of a carbohydrate exhibits a pharmaceutically acceptable shelf-life at a temperature up to 40° C. for 3 months at 75% RH, wherein, a minimal or no loss in potency/assay compared to the solution wherein higher quantities of same carbohydrates have been employed, as taught by Schridde et al in EP 1466599.

It might be mentioned that a solution of Oxaliplatin in water on storage invariably results in formation of certain degradation products as well as impurities, both known, characterized and reported in the Pharmacopoeial Forums as well as those, which have not been characterized or are unknown.

The known degradation products/impurities of oxaliplatin referred to in European pharmacopoeial monograph are the following:
1) Oxalic acid referred to as Impurity 'A'
2) (SP-4-2)-diaqual[(1R,2R)-cyclohexane-1,2diamine-κN, κN']platinum(diaquo diamino cyclohexane platinum) referred to as Impurity 'B'
3) (OC-6-33)-[(1R,2R)-cyclohexane-1,2 diamine--κN,κN'][ethanediota(2-)-κO¹, -κO²]dihydroxyplatinum referred to as Impurity 'C'
4) (SP-4-2)-diaqual[(1S,2S)-cyclohexane-1,2diamine-κN, κN'][ethanediota(2-)-κO¹, -κO²]platinum (S,S-enantiomer of oxaliplatin) referred to as Impurity 'D'
5) SP-4-2)-di-μ-oxobis [(1R, 2R)-cyclohexane-1,2diamine-κN,κN']diplatinum (diaquodiaminocyclohexane platinum dimer) referred to as Impurity 'E'; whose chemical structures are given below:

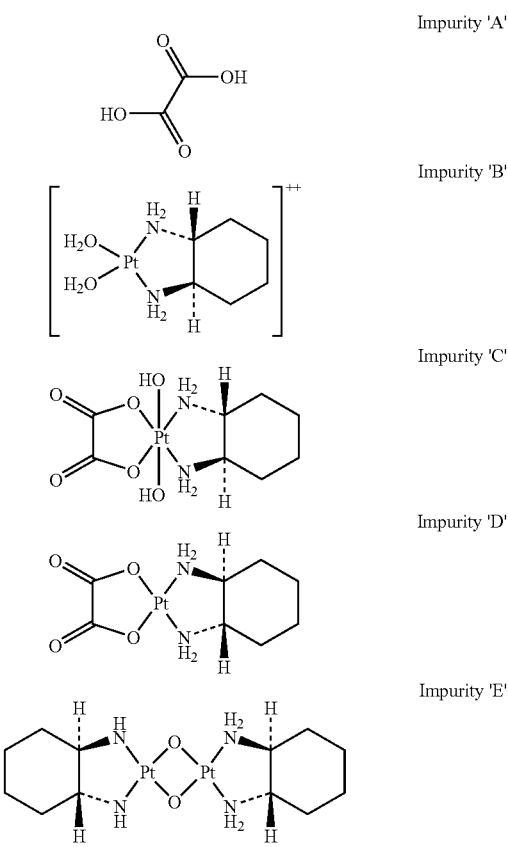

It has been found that when a catalytic amount of a carbohydrate is employed, the level of total impurities decreases as compared to when a higher concentration of 5% to 50% of a carbohydrate is used.

Also, the formulation remains stable over a long period of time at a temperature up to 40° C. for 3 months at 75% RH as compared to the teachings of the prior art, EP 1466599, which advocates a cold storage at 2-8° C. for long term stability of oxaliplatin solution concentrates. (Please refer Table 6 of EP 1466599).

In addition, EP 1466599 teaches that reducing the pH of the solution by adding acids or buffers further stabilizes the solution. However, the addition of acid along with the higher amount of glucose does not significantly reduce the decomposition of the active substance in the Oxaliplatin solution concentrate. (Please refer Table 7 of EP 1466599).

Lastly, but not the least an aqueous ready-to-use solution of oxaliplatin containing catalytic amount of carbohydrate of the present invention is found to exhibit negligible loss in potency as compared to such aqueous solutions wherein no additive is added as taught in U.S. Pat. No. 5,716,988.

The advantages and superiority of the ready-to-use aqueous solution formulation containing a catalytic amount of a carbohydrate as per the present invention over ready-to-use aqueous solution of Oxaliplatin containing no carbohydrate or no acid or large amounts of carbohydrates could be best understood from a comparison given in Table I.

TABLE I

Stability Studies of an Aqueous Ready-to-Use Solution of Oxaliplatin Containing Catalytic amount of a Carbohydrate as per the Present Invention in Comparison to those Containing No Carbohydrate or Higher Concentration of a Carbohydrate and/or an Acid

| Sr. No. | Nature of Additive | Concentration (%) | Storage Condition at 75% RH of oxaliplatin solutions | Assay (%) | Impurities (% w/w) | | | | | |
|---|---|---|---|---|---|---|---|---|---|---|
| | | | | | A | B | C | Highest Unknown | Total Unknown | Total Impurities |
| 1 | None (As taught in U.S. Pat. No. 5,716,988) | — | Initial | 102.1 | 0.280 | 0.300 | 0.004 | 0.174 | 0.176 | 0.760 |
| | | | 1M/40° C. | 100.9 | 0.447 | 0.054 | 0.009 | 0.041 | 0.056 | 0.566 |
| | | | 2M/40° C. | 99.2 | 0.220 | 0.015 | ND | 0.101 | 0.133 | 0.368 |
| | | | 3M/40° C. | 99.3 | 0.350 | 0.240 | 0.005 | 0.161 | 0.174 | 0.769 |
| 2 | Carbohydrate Lactose (As taught in EP 1,466,599) | 5 | Initial | 105.3 | 0.175 | 0.032 | 0.362 | 0.059 | 0.247 | 0.815 |
| | | | 1M/40° C. | 101.3 | 0.190 | 0.030 | 0.833 | 0.261 | 0.607 | 1.660 |
| | | | 2M/40° C. | 101.8 | 0.198 | 0.024 | 1.023 | 0.514 | 0.934 | 2.179 |
| | | | 3M/40° C. | 100.8 | 0.215 | 0.031 | 1.111 | 0.792 | 1.326 | 2.682 |
| 3 | Carbohydrate (Lactose) + Acid (Tartaric acid) (As taught in EP 1,466,599) | 5 + 1 | Initial | 96.9 | 0.393 | 0.023 | 0.258 | 0.099 | 0.494 | 1.168 |
| | | | 1M/40° C. | 96.6 | 0.389 | 0.029 | 0.311 | 0.127 | 0.703 | 1.432 |
| | | | 2M/40° C. | 96.9 | 0.403 | 0.032 | 0.325 | 0.186 | 0.734 | 1.494 |
| | | | 3M/40° C. | 92.2 | 0.419 | 0.024 | 0.329 | 0.255 | 0.891 | 1.663 |
| 4 | Carbohydrate- (Lactose) In Catalytic Amount (As per the present invention) | 0.0010 | Initial | 97.6 | 0.200 | 0.250 | 0.019 | 0.159 | 0.250 | 0.719 |
| | | | 1M/40° C. | 95.9 | 0.233 | 0.240 | 0.006 | 0.126 | 0.245 | 0.731 |
| | | | 2M/40° C. | 97.2 | 0.310 | 0.270 | 0.003 | 0.142 | 0.236 | 0.819 |
| | | | 3M/40° C. | 98.6 | 0.290 | 0.220 | 0.003 | 0.019 | 0.055 | 0.568 |
| | | 0.0020 | Initial | 97.7 | 0.168 | 0.250 | 0.005 | 0.151 | 0.267 | 0.712 |
| | | | 1M/40° C. | 96.6 | 0.234 | 0.210 | 0.006 | 0.139 | 0.243 | 0.709 |
| | | | 2M/40° C. | 97.9 | 0.260 | 0.260 | 0.004 | 0.133 | 0.224 | 0.748 |
| | | | 3M/40° C. | 98.6 | 0.340 | 0.310 | 0.002 | 0.028 | 0.051 | 0.703 |
| | | 0.0025 | Initial | 99.6 | 0.164 | 0.260 | 0.005 | 0.104 | 0.192 | 0.657 |
| | | | 1M/40° C. | 98.5 | 0.226 | 0.220 | 0.004 | 0.125 | 0.212 | 0.666 |
| | | | 2M/40° C. | 99.5 | 0.250 | 0.270 | 0.003 | 0.140 | 0.254 | 0.777 |
| | | | 3M/40° C. | 100.5 | 0.270 | 0.230 | 0.003 | 0.123 | 0.129 | 0.632 |
| | | 0.0050 | Initial | 97.3 | 0.165 | 0.280 | 0.013 | 0.137 | 0.235 | 0.738 |
| | | | 1M/40° C. | 96.8 | 0.244 | 0.210 | 0.004 | 0.135 | 0.218 | 0.692 |
| | | | 2M/40° C. | 98.2 | 0.260 | 0.270 | 0.004 | 0.126 | 0.230 | 0.764 |
| | | | 3M/40° C. | 99.4 | 0.320 | 0.230 | 0.005 | 0.134 | 0.149 | 0.704 |
| | | 0.010 | Initial | 99.9 | 0.184 | 0.290 | 0.016 | 0.125 | 0.220 | 0.756 |
| | | | 1M/40° C. | 98.0 | 0.245 | 0.230 | 0.004 | 0.134 | 0.183 | 0.637 |
| | | | 2M/40° C. | 99.6 | 0.250 | 0.290 | 0.004 | 0.143 | 0.259 | 0.803 |
| | | | 3M/40° C. | 100.6 | 0.310 | 0.180 | 0.006 | 0.149 | 0.170 | 0.666 |
| | | 0.020 | Initial | 98.8 | 0.160 | 0.250 | 0.013 | 0.118 | 0.210 | 0.633 |
| | | | 1M/40° C. | 98.6 | 0.220 | 0.240 | 0.006 | 0.099 | 0.194 | 0.600 |
| | | | 2M/40° C. | 99.8 | 0.230 | 0.280 | 0.006 | 0.122 | 0.229 | 0.745 |
| | | | 3M/40° C. | 100.8 | 0.300 | 0.210 | 0.008 | 0.166 | 0.181 | 0.699 |
| | | 0.03 | Initial | 108.1 | 0.16 | 0.29 | ND | 0.01 | 0.02 | 0.52 |
| | | | 1M/40° C. | 109.4 | 0.22 | 0.19 | ND | 0.02 | 0.05 | 0.56 |
| | | | 2M/40° C. | 106.7 | 0.26 | 0.21 | 0.01 | 0.05 | 0.08 | 0.68 |
| | | | 3M/40° C. | 107.9 | 0.25 | 0.18 | 0.01 | 0.07 | 0.12 | 0.67 |
| | | 0.05 | Initial | 107.1 | 0.14 | 0.29 | ND | 0.01 | 0.03 | 0.48 |
| | | | 1M/40° C. | 106.7 | 0.18 | 0.21 | 0.04 | 0.09 | 0.14 | 0.62 |
| | | | 2M/40° C. | 105.4 | 0.20 | 0.21 | 0.01 | 0.05 | 0.07 | 0.56 |
| | | | 3M/40° C. | 105.8 | 0.20 | 0.17 | 0.01 | 0.06 | 0.11 | 0.56 |
| 5 | Carbohydrate- (Dextrose) In Catalytic Amount (As per the present Invention) | 0.0010 | Initial | 100.2 | 0.250 | 0.320 | 0.002 | 0.097 | 0.098 | 0.670 |
| | | | 1M/40° C. | 99.7 | 0.260 | 0.003 | 0.003 | ND | ND | ND |
| | | | 2M/40° C. | 100.4 | 0.320 | 0.00 | 0.00 | ND | ND | 0.520 |
| | | | 3M/40° C. | 98.6 | 0.200 | ND | ND | 0.020 | 0.050 | |
| | | 0.0020 | Initial | 101.2 | 0.180 | 0.310 | 0.001 | 0.120 | 0.121 | 0.612 |
| | | | 1M/40° C. | 101.1 | 0.270 | 0.220 | 0.002 | ND | ND | 0.492 |
| | | | 2M/40° C. | 101.7 | 0.31 | 0.230 | 0.00 | ND | ND | ND |
| | | | 3M/40° C. | 101.8 | 0.200 | 0.190 | ND | 0.020 | 0.040 | 0.510 |
| | | 0.0025 | Initial | 100.0 | 0.210 | 0.310 | 0.002 | 0.099 | 0.114 | 0.636 |
| | | | 1M/40° C. | 99.1 | 0.260 | 0.210 | 0.003 | 0.022 | 0.029 | 0.502 |
| | | | 2M/40° C. | 99.8 | 0.300 | 0.200 | 0.000 | ND | ND | ND |
| | | | 3M/40° C. | 98.9 | 0.210 | 0.180 | ND | 0.090 | 0.090 | 0.560 |
| | | 0.0050 | Initial | 101.4 | 0.150 | 0.330 | 0.002 | 0.079 | 0.080 | 0.562 |
| | | | 1M/40° C. | 101.1 | 0.270 | 0.220 | 0.003 | 0.012 | 0.019 | 0.512 |
| | | | 2M/40° C. | 101.2 | 0.28 | 0.21 | 0.000 | ND | ND | ND |
| | | | 3M/40° C. | 102.2 | 0.200 | 0.220 | ND | 0.020 | 0.050 | 0.530 |
| | | 0.010 | Initial | 101.4 | 0.170 | 0.300 | 0.003 | 0.074 | 0.075 | 0.548 |
| | | | 1M/40° C. | 100.9 | 0.270 | 0.220 | 0.002 | 0.005 | 0.005 | 0.497 |
| | | | 2M/40° C. | 101.5 | 0.290 | 0.210 | 0.010 | ND | ND | ND |
| | | | 3M/40° C. | 101.7 | 0.200 | 0.170 | ND | 0.030 | 0.080 | 0.520 |

TABLE I-continued

Stability Studies of an Aqueous Ready-to-Use Solution of Oxaliplatin
Containing Catalytic amount of a Carbohydrate as per the Present Invention in
Comparison to those Containing No Carbohydrate or Higher Concentration of a
Carbohydrate and/or an Acid

| Sr. No. | Nature of Additive | Additive Concentration (%) | Storage Condition at 75% RH of oxaliplatin solutions | Assay (%) | Impurities (% w/w) | | | | | |
|---|---|---|---|---|---|---|---|---|---|---|
| | | | | | A | B | C | Highest Unknown | Total Unknown | Total Impurities |
| | | 0.020 | Initial | 100.9 | 0.170 | 0.310 | 0.003 | 0.090 | 0.091 | 0.574 |
| | | | 1M/40° C. | 100.5 | 0.340 | 0.220 | 0.004 | 0.013 | 0.019 | 0.583 |
| | | | 2M/40° C. | 100.6 | 0.280 | 0.230 | 0.010 | ND | ND | ND |
| | | | 3M/40° C. | 101.0 | 0.200 | 0.190 | 0.010 | 0.030 | 0.100 | 0.570 |
| 6 | Carbohydrate- (Sucrose) In Catalytic Amount (As per the present Invention) | 0.0010 | Initial | 99.8 | 0.190 | 0.330 | 0.002 | 0.067 | 0.067 | 0.589 |
| | | | 1M/40° C. | 99.2 | 0.260 | 0.230 | 0.002 | 0.017 | 0.017 | 0.509 |
| | | | 2M/40° C. | 100.1 | 0.280 | 0.250 | 0.000 | ND | ND | ND |
| | | | 3M/40° C. | 99.2 | 0.200 | 0.210 | ND | 0.020 | 0.030 | 0.520 |
| | | 0.0020 | Initial | 101.3 | 0.150 | 0.330 | 0.002 | 0.061 | 0.061 | 0.543 |
| | | | 1M/40° C. | 100.8 | 0.50 | 0.220 | 0.002 | 0.016 | 0.029 | 0.501 |
| | | | 2M/40° C. | 101.8 | 0.260 | 0.250 | 0.000 | ND | ND | ND |
| | | | 3M/40° C. | 101.8 | 0.180 | 0.210 | ND | 0.020 | 0.040 | 0.510 |
| | | 0.0025 | Initial | 100.8 | 0.210 | 0.310 | 0.002 | 0.099 | 0.114 | 0.636 |
| | | | 1M/40° C. | 99.1 | 0.260 | 0.210 | 0.003 | 0.022 | 0.029 | 0.502 |
| | | | 2M/40° C. | 99.8 | 0.300 | 0.200 | 0.000 | ND | ND | ND |
| | | | 3M/40° C. | 98.9 | 0.210 | 0.180 | ND | 0.030 | 0.090 | 0.560 |
| | | 0.0050 | Initial | 99.0 | 0.150 | 0.340 | 0.002 | 0.060 | 0.060 | 0.552 |
| | | | 1M/40° C. | 99.2 | 0.280 | 0.240 | 0.001 | 0.008 | 0.008 | 0.529 |
| | | | 2M/40° C. | 99.5 | 0.270 | 0.260 | 0.000 | ND | ND | ND |
| | | | 3M/40° C. | 99.8 | 0.210 | 0.200 | ND | 0.020 | 0.030 | 0.530 |
| | | 0.010 | Initial | 100.5 | 0.210 | 0.330 | 0.002 | 0.055 | 0.055 | 0.597 |
| | | | 1M/40° C. | 99.7 | 0.280 | 0.260 | 0.002 | 0.011 | 0.011 | 0.533 |
| | | | 2M/40° C. | 100.8 | 0.250 | 0.270 | 0.000 | ND | ND | ND |
| | | | 3M/40° C. | 100.3 | 0.190 | 0.170 | ND | 0.020 | 0.030 | 0.470 |
| | | 0.020 | Initial | 102.0 | 0.200 | 0.350 | 0.002 | 0.065 | 0.065 | 0.617 |
| | | | 1M/40° C. | 100.5 | 0.260 | 0.240 | 0.002 | 0.009 | 0.009 | 0.511 |
| | | | 2M/40° C. | 101.7 | 0.270 | 0.280 | 0.000 | ND | ND | ND |
| | | | 3M/40° C. | 100.7 | 0.190 | 0.190 | ND | 0.020 | 0.040 | 0.500 |

*ND: Not Determined

Further, the effect in assay and level of impurities on utilizing a carbohydrate at a concentration higher than 0.02 w/v solution of oxaliplatin was also studied which indicates that when the carbohydrate, especially lactose is employed in a concentration ranging from 0.05%-5% w/v of the solution is found to result in gradual drop in assay as well as gradual increase in level of degradation products. These are summarized in Table II.

TABLE II

Comparison of Stability of an Aqueous Ready-to-Use Oxaliplatin Solutions
containing various amounts of Carbohydrate ("Catalytic Amount" as per the
present invention vis-a-vis "Non-catalytic Amount" as per the Prior Art)

| Selected Auxiliary Additives | Carbohydrate Concentration (%) | Storage Condition at 75% RH of oxaliplatin solutions | Assay (%) | Impurities (% w/w) | | | | | |
|---|---|---|---|---|---|---|---|---|---|
| | | | | A | B | C | Highest Unknown | Total Unknown | Total Impurities |
| Lactose | 0.0010 | Initial | 97.6 | 0.200 | 0.250 | 0.019 | 0.159 | 0.250 | 0.719 |
| | | 1M/40° C. | 95.9 | 0.233 | 0.240 | 0.006 | 0.126 | 0.245 | 0.731 |
| | | 2M/40° C. | 97.2 | 0.310 | 0.270 | 0.003 | 0.142 | 0.236 | 0.819 |
| | | 3M/40° C. | 98.6 | 0.290 | 0.220 | 0.003 | 0.019 | 0.055 | 0.568 |
| Lactose | 0.0020 | Initial | 97.7 | 0.168 | 0.250 | 0.005 | 0.151 | 0.267 | 0.712 |
| | | 1M/40° C. | 96.6 | 0.234 | 0.210 | 0.006 | 0.139 | 0.243 | 0.709 |
| | | 2M/40° C. | 97.9 | 0.260 | 0.260 | 0.004 | 0.133 | 0.224 | 0.748 |
| | | 3M/40° C. | 98.6 | 0.340 | 0.310 | 0.002 | 0.028 | 0.051 | 0.703 |
| Lactose | 0.0025 | Initial | 99.6 | 0.164 | 0.260 | 0.005 | 0.104 | 0.192 | 0.657 |
| | | 1M/40° C. | 98.5 | 0.226 | 0.220 | 0.004 | 0.125 | 0.212 | 0.666 |
| | | 2M/40° C. | 99.5 | 0.250 | 0.270 | 0.003 | 0.140 | 0.254 | 0.777 |
| | | 3M/40° C. | 100.5 | 0.270 | 0.230 | 0.003 | 0.123 | 0.129 | 0.632 |

TABLE II-continued

Comparison of Stability of an Aqueous Ready-to-Use Oxaliplatin Solutions containing various amounts of Carbohydrate ("Catalytic Amount" as per the present invention vis-a-vis "Non-catalytic Amount" as per the Prior Art)

| Selected Auxiliary Additives | Carbohydrate Concentration (%) | Storage Condition at 75% RH of oxaliplatin solutions | Assay (%) | Impurities (% w/w) | | | | | |
|---|---|---|---|---|---|---|---|---|---|
| | | | | A | B | C | Highest Unknown | Total Unknown | Total Impurities |
| Lactose | 0.0050 | Initial | 97.3 | 0.165 | 0.280 | 0.013 | 0.137 | 0.235 | 0.738 |
| | | 1M/40° C. | 96.8 | 0.244 | 0.210 | 0.004 | 0.135 | 0.218 | 0.692 |
| | | 2M/40° C. | 98.2 | 0.260 | 0.270 | 0.004 | 0.126 | 0.230 | 0.764 |
| | | 3M/40° C. | 99.4 | 0.320 | 0.230 | 0.005 | 0.134 | 0.149 | 0.704 |
| Lactose | 0.010 | Initial | 99.9 | 0.184 | 0.290 | 0.016 | 0.125 | 0.220 | 0.756 |
| | | 1M/40° C. | 98.0 | 0.245 | 0.230 | 0.004 | 0.134 | 0.183 | 0.637 |
| | | 2M/40° C. | 99.6 | 0.250 | 0.290 | 0.004 | 0.143 | 0.259 | 0.803 |
| | | 3M/40° C. | 100.6 | 0.310 | 0.180 | 0.006 | 0.149 | 0.170 | 0.666 |
| Lactose | 0.020 | Initial | 98.8 | 0.160 | 0.250 | 0.013 | 0.118 | 0.210 | 0.633 |
| | | 1M/40° C. | 98.6 | 0.220 | 0.240 | 0.006 | 0.099 | 0.194 | 0.600 |
| | | 2M/40° C. | 99.8 | 0.230 | 0.280 | 0.006 | 0.122 | 0.229 | 0.745 |
| | | 3M/40° C. | 100.8 | 0.300 | 0.210 | 0.008 | 0.166 | 0.181 | 0.699 |
| Lactose | 0.03 | Initial | 108.1 | 0.16 | 0.29 | ND | 0.01 | 0.02 | 0.52 |
| | | 1M/40° C. | 109.4 | 0.22 | 0.19 | ND | 0.02 | 0.05 | 0.56 |
| | | 2M/40° C. | 106.7 | 0.26 | 0.21 | 0.01 | 0.05 | 0.08 | 0.68 |
| | | 3M/40° C. | 107.9 | 0.25 | 0.18 | 0.01 | 0.07 | 0.12 | 0.67 |
| Lactose | 0.045 | Initial | 99.36 | 0.15 | 0.34 | ND | 0.08 | 0.12 | 0.63 |
| | | 1M/40° C. | 96.7 | 0.23 | 0.14 | 0.01 | 0.13 | 0.20 | 0.60 |
| | | 2M/40° C. | 98.94 | 0.24 | 0.13 | 0.01 | 0.12 | 0.20 | 0.60 |
| | | 3M/40° C. | ND | ND | ND | ND | ND | ND | ND |
| Lactose | 0.05 | Initial | 107.1 | 0.14 | 0.29 | ND | 0.01 | 0.03 | 0.48 |
| | | 1M/40° C. | 106.7 | 0.18 | 0.21 | 0.04 | 0.09 | 0.14 | 0.62 |
| | | 2M/40° C. | 105.4 | 0.20 | 0.21 | 0.01 | 0.05 | 0.07 | 0.56 |
| | | 3M/40° C. | 105.8 | 0.20 | 0.17 | 0.01 | 0.06 | 0.11 | 0.56 |
| Lactose | 0.2 | Initial | 107.2 | 0.15 | 0.31 | ND | 0.01 | 0.02 | 0.52 |
| | | 1M/40° C. | 106.2 | 0.18 | 0.18 | 0.01 | 0.03 | 0.06 | 0.49 |
| | | 2M/40° C. | 106.1 | 0.20 | 0.18 | 0.03 | 0.12 | 0.15 | 0.61 |
| | | 3M/40° C. | 106.1 | 0.22 | 0.16 | 0.04 | 0.17 | 0.24 | 0.70 |
| Lactose | 0.3 | Initial | 108.3 | 0.140 | 0.300 | ND | 0.010 | 0.020 | 0.490 |
| | | 1M/40° C. | 108.8 | 0.200 | 0.230 | 0.020 | 0.050 | 0.090 | 0.610 |
| | | 2M/40° C. | 107.5 | 0.190 | 0.170 | 0.040 | 0.140 | 0.170 | 0.610 |
| | | 3M/40° C. | 107.4 | 0.23 | 0.15 | 0.50 | 0.27 | 0.35 | 0.82 |
| Lactose | 0.5 | Initial | 107.2 | 0.140 | 0.290 | ND | 0.010 | 0.030 | 0.480 |
| | | 1M/40° C. | 106.7 | 0.180 | 0.210 | 0.040 | 0.090 | 0.140 | 0.620 |
| | | 2M/40° C. | 104.1 | 0.210 | 0.170 | 0.080 | 0.230 | 0.270 | 0.760 |
| | | 3M/40° C. | 105.4 | 0.23 | 0.13 | 0.080 | 0.42 | 0.52 | 0.98 |
| Lactose | 2.0 | Initial | 104.6 | 0.140 | 0.280 | 0.010 | 0.030 | 0.070 | 0.510 |
| | | 1M/40° C. | 104.2 | 0.180 | 0.170 | 0.120 | 0.130 | 0.200 | 0.680 |
| | | 2M/40° C. | 102.8 | 0.200 | 0.150 | 0.220 | 0.450 | 0.550 | 1.120 |
| | | 3M/40° C. | 103.1 | 0.22 | 0.11 | 0.24 | 0.66 | 0.81 | 1.38 |
| Lactose | 3.0 | Initial | 108.4 | 0.140 | 0.260 | 0.010 | 0.030 | 0.080 | 0.500 |
| | | 1M/40° C. | 108.4 | 0.020 | 0.210 | 0.160 | 0.050 | 0.090 | 0.730 |
| | | 2M/40° C. | 107.5 | 0.210 | 0.150 | 0.280 | 0.480 | 0.560 | 1.200 |
| | | 3M/40° C. | 107 | 0.23 | 0.15 | 0.29 | 0.75 | 0.93 | 1.60 |
| Lactose | 4.5 | Initial | 100.7 | 0.14 | 0.22 | 0.01 | 0.09 | 0.13 | 0.50 |
| | | 1M/40° C. | 99.38 | 0.24 | 0.14 | 0.15 | 0.09 | 0.28 | 0.81 |
| | | 2M/40° C. | 99.22 | 0.21 | 0.15 | 0.22 | 0.29 | 0.54 | 1.12 |
| | | 3M/40° C. | ND | ND | ND | ND | ND | ND | ND |
| Lactose | 5 | Initial | 105.1 | 0.175 | 0.032 | 0.362 | 0.059 | 0.247 | 0.815 |
| | | 1M/40° C. | 101.2 | 0.190 | 0.030 | 0.833 | 0.261 | 0.607 | 1.660 |
| | | 2M/40° C. | 101.8 | 0.198 | 0.024 | 1.023 | 0.514 | 0.934 | 2.179 |
| | | 3M/40° C. | 100.8 | 0.215 | 0.031 | 1.111 | 0.792 | 1.326 | 2.682 |

*ND: Not Determined

The present invention is detailed hereinbelow.

As mentioned hereinbefore, the present invention is directed to a storage stable ready-to-use aqueous solution of Oxaliplatin wherein the stabilization is achieved through an addition of catalytic amount of an additive, in particular a catalytic amount of a carbohydrate and a method for preparation of such stable aqueous ready-to-use solutions. Again as discussed hereinbefore, minimization of degradation products as well as enhanced stability could be achieved through utilization of a catalytic amount of a carbohydrate.

Suitable carbohydrates that can be employed are those that are not only routinely used in the preparation of pharmaceutical compositions but are also accepted by regulatory and health authorities.

Suitable carbohydrates include lactose, glucose, sucrose, and dextrose etc., of which lactose is the most preferred carbohydrate.

Typically the carbohydrate can be employed in a concentration ranging from 0.0010% to 0.020% w/v solution of oxaliplatin, preferably 0.0025% w/v solution of oxaliplatin. Such a pharmaceutical composition, since being meant for IV Infusion is typically a sterile solution contained in a suitable vial, which needless to mention is prepared under aseptic conditions.

Typical glass vials that can be utilized to contain the stable ready-to-use aqueous solution formulation of Oxaliplatin are normal glass vials, which are not pretreated/special grade/ types of glass, even though, such glass vials could also be used to contain the pharmaceutical composition of oxaliplatin.

Vials made of USP Type I glass, commonly known as "normal hydrolytic class-I glass" or borosilicate glass are corning® Pyrex® 7740 and Wheaton 180, 200, and 400. Again, typically the glass vials can be sealed with both normal as well as special stoppers, the former being adequate.

In a specific embodiment, a stable composition would contain 5-mg/ml solution of Oxaliplatin in water and a catalytic amount of carbohydrate in glass vials typically sealed with elastomeric stoppers and aluminium flip-off seals.

A typical method for preparation of ready-to-use aqueous solution formulation of Oxaliplatin comprises dissolving known amount of oxaliplatin in water to which weighed quantity of carbohydrate is added. The amount of carbohydrate added is in the range of 0.0010% to 0.05% w/v with respect to the solution. The resultant solution is filtered through suitable grade filter membrane under aseptic conditions, filled into vials and stoppered and sealed with aluminium flip-off seals.

The following examples describe the invention in more detail concerning the injectable preparation according to the invention, its manufacture and comparison of its stability.

These are offered for illustrative purposes only, and are not intended to limit the scope of the present invention in any way.

Experimental

1) Preparation of Aqueous Solution of Oxaliplatin:

To double distilled water taken in a glass container, an amount of Oxaliplatin necessary for obtaining a concentration of 5 mg/ml is added and stirred at 30-35° C. (maintained using suitable temperature control device) until the entire drug is dissolved.

Separately stock solutions of concentrations of the respective carbohydrates viz., lactose, Dextrose and Sucrose were prepared in double distilled water in volumetric flasks. Sufficient quantities of these stock solutions were added to the Oxaliplatin solutions, so that a final concentration of the respective carbohydrate in the solution is 0.001%, 0.002%, 0.0025%, 0.005%, 0.01% and 0.02% w/v solution of Oxaliplatin. Further, double distilled water is added to bring the solutions to their final volume. The resultant solutions were filtered through suitable grade filter membrane.

2) Packaging

Volumes of 10 ml of the solution were distributed into Type I colorless glass vials. The vials were immediately stoppered with rubber stoppers and sealed with aluminium flip-off overseal.

3) Stability Test

The solution in the vials stored in inverted configuration were subjected to accelerated conditions of 40° C./75% relative humidity for up to 3 months. The stability data, obtained using high performance liquid chromatography (HPLC) is used to determine potency and impurity profile. Furthermore, the carbohydrate content of the respective carbohydrates in these solutions were determined using ion chromatography "Dionex" at initial time point and after 3 months duration at accelerated conditions. The appearance of the formulations was assessed at the initial, 1-month, 2 months and 3 months time point. For the sake of convenience, Table I is summarized again in the following examples (1, 2 and 3) hereinbelow.

These corroborates with the findings of the present invention that as the concentration of carbohydrate is increased, the level of impurities increases. At higher concentrations of carbohydrate, the level of impurities attained within one-month duration equals or exceeds the level obtained with the catalytic amount of carbohydrate of the present invention even after three months.

EXAMPLE-1

Comparative Data of Oxaliplatin Solution Containing Various Concentration of Lactose An aqueous solution of Oxaliplatin of 5 mg/ml was prepared using double distilled water contained in a glass container and added the required quantity of lactose followed by stirring at 30-35° C. until the complete dissolution of drug occurs. The stock solution of carbohydrates viz., lactose was added in the above solution to get final concentrations. The results of stability of such solutions are summarized in Table-III.

TABLE III

Stability Data of an Aqueous Ready-to-Use Oxaliplatin Solutions containing Catalytic Amounts of Lactose

| Selected Auxiliary Additives | Carbohydrate Concentration (%) | Condition | Assay (%) | Impurities (% w/w) | | | | | |
|---|---|---|---|---|---|---|---|---|---|
| | | | | A | B | C | Highest Unknown | Total Unknown | Total Impurities |
| Lactose | 0.0010 | initial | 97.6 | 0.200 | 0.250 | 0.019 | 0.159 | 0.250 | 0.719 |
| | | 1M/40° C. | 95.9 | 0.233 | 0.240 | 0.006 | 0.126 | 0.245 | 0.731 |
| | | 2M/40° C. | 97.2 | 0.310 | 0.270 | 0.003 | 0.142 | 0.236 | 0.819 |
| | | 3M/40° C. | 98.6 | 0.290 | 0.220 | 0.003 | 0.019 | 0.055 | 0.568 |
| Lactose | 0.0020 | Initial | 97.7 | 0.168 | 0.250 | 0.005 | 0.151 | 0.267 | 0.712 |
| | | 1M/40° C. | 96.6 | 0.234 | 0.210 | 0.006 | 0.139 | 0.243 | 0.709 |
| | | 2M/40° C. | 97.9 | 0.260 | 0.260 | 0.004 | 0.133 | 0.224 | 0.748 |
| | | 3M/40° C. | 98.6 | 0.340 | 0.310 | 0.002 | 0.028 | 0.051 | 0.703 |
| Lactose | 0.0025 | Initial | 99.6 | 0.164 | 0.260 | 0.005 | 0.104 | 0.192 | 0.657 |
| | | 1M/40° C. | 98.5 | 0.226 | 0.220 | 0.004 | 0.125 | 0.212 | 0.666 |

TABLE III-continued

Stability Data of an Aqueous Ready-to-Use Oxaliplatin Solutions containing Catalytic Amounts of Lactose

| Selected Auxiliary Additives | Carbohydrate Concentration (%) | Condition | Assay (%) | Impurities (% w/w) | | | | | |
|---|---|---|---|---|---|---|---|---|---|
| | | | | A | B | C | Highest Unknown | Total Unknown | Total Impurities |
| | | 2M/40° C. | 99.5 | 0.250 | 0.270 | 0.003 | 0.140 | 0.254 | 0.777 |
| | | 3M/40° C. | 100.5 | 0.270 | 0.230 | 0.003 | 0.123 | 0.129 | 0.632 |
| Lactose | 0.0050 | Initial | 97.3 | 0.165 | 0.280 | 0.013 | 0.137 | 0.235 | 0.738 |
| | | 1M/40° C. | 96.8 | 0.244 | 0.210 | 0.004 | 0.135 | 0.218 | 0.692 |
| | | 2M/40° C. | 98.2 | 0.260 | 0.270 | 0.004 | 0.126 | 0.230 | 0.764 |
| | | 3M/40° C. | 99.4 | 0.320 | 0.230 | 0.005 | 0.134 | 0.149 | 0.704 |
| Lactose | 0.010 | Initial | 99.9 | 0.184 | 0.290 | 0.016 | 0.125 | 0.220 | 0.756 |
| | | 1M/40° C. | 98.0 | 0.245 | 0.230 | 0.004 | 0.134 | 0.183 | 0.637 |
| | | 2M/40° C. | 99.6 | 0.250 | 0.290 | 0.004 | 0.143 | 0.259 | 0.803 |
| | | 3M/40° C. | 100.6 | 0.310 | 0.180 | 0.006 | 0.149 | 0.170 | 0.666 |
| Lactose | 0.020 | Initial | 98.8 | 0.160 | 0.250 | 0.013 | 0.118 | 0.210 | 0.633 |
| | | 1M/40° C. | 98.6 | 0.220 | 0.240 | 0.006 | 0.099 | 0.194 | 0.600 |
| | | 2M/40° C. | 99.8 | 0.230 | 0.280 | 0.006 | 0.122 | 0.229 | 0.745 |
| | | 3M/40° C. | 100.8 | 0.300 | 0.210 | 0.008 | 0.166 | 0.181 | 0.699 |

EXAMPLE-2

Comparative Data of Oxaliplatin Solution Containing Various Concentration of Dextrose An aqueous solution of Oxaliplatin of 5 mg/ml was prepared using double distilled water contained in a glass container and added the required quantity of dextrose followed by stirring at 30-35° C. until the complete dissolution of drug occurs. The stock solution of carbohydrates viz., dextrose was added in the above solution to get final concentrations.

The results of stability of such solutions are summarized in Table-IV.

EXAMPLE-3

Comparative Data of Oxaliplatin Solution Containing Various Concentration of Sucrose An aqueous solution of Oxaliplatin of 5 mg/ml was prepared using double distilled water contained in a glass container and added the required quantity of sucrose followed by stirring at 30-35° C. until the complete dissolution of drug occurs. The stock solution of carbohydrates viz., sucrose was added in the above solution to get final concentrations. The results of stability of such solutions are summarized in Table-V.

TABLE IV

Stability Data of an Aqueous Ready-to-Use Oxaliplatin Solutions containing Catalytic Amounts of Dextrose

| Selected Auxiliary Additives | Carbohydrate Concentration (%) | Condition | Assay (%) | Impurities (% w/w) | | | | | |
|---|---|---|---|---|---|---|---|---|---|
| | | | | A | B | C | Highest Unknown | Total Unknown | Total Impurities |
| Dextrose | 0.0010 | Initial | 100.2 | 0.250 | 0.320 | 0.002 | 0.097 | 0.098 | 0.670 |
| | | 1M/40° C. | 99.7 | 0.260 | 0.003 | 0.003 | ND | ND | 0.473 |
| | | 2M/40° C. | 100.4 | 0.320 | 0.00 | 0.00 | NA | NA | NA |
| | | 3M/40° C. | 98.6 | 0.200 | ND | ND | 0.020 | 0.050 | 0.520 |
| Dextrose | 0.0020 | Initial | 101.2 | 0.180 | 0.310 | 0.001 | 0.120 | 0.121 | 0.612 |
| | | 1M/40° C. | 101.1 | 0.270 | 0.220 | 0.002 | ND | ND | 0.492 |
| | | 2M/40° C. | 101.7 | 0.31 | 0.230 | 0.00 | NA | NA | NA |
| | | 3M/40° C. | 101.8 | 0.200 | 0.190 | ND | 0.020 | 0.040 | 0.510 |
| Dextrose | 0.0025 | Initial | 100.0 | 0.210 | 0.310 | 0.002 | 0.099 | 0.114 | 0.636 |
| | | 1M/40° C. | 99.1 | 0.260 | 0.210 | 0.003 | 0.022 | 0.029 | 0.502 |
| | | 2M/40° C. | 99.8 | 0.300 | 0.200 | 0.000 | NA | NA | NA |
| | | 3M/40° C. | 98.9 | 0.210 | 0.180 | ND | 0.090 | 0.090 | 0.560 |
| Dextrose | 0.0050 | Initial | 101.4 | 0.150 | 0.330 | 0.002 | 0.079 | 0.080 | 0.562 |
| | | 1M/40° C. | 101.1 | 0.270 | 0.220 | 0.003 | 0.012 | 0.019 | 0.512 |
| | | 2M/40° C. | 101.2 | 0.28 | 0.21 | 0.000 | NA | NA | NA |
| | | 3M/40° C. | 102.2 | 0.200 | 0.220 | ND | 0.020 | 0.050 | 0.530 |
| Dextrose | 0.010 | Initial | 101.4 | 0.170 | 0.300 | 0.003 | 0.074 | 0.075 | 0.548 |
| | | 1M/40° C. | 100.9 | 0.270 | 0.220 | 0.002 | 0.005 | 0.005 | 0.497 |
| | | 2M/40° C. | 101.5 | 0.290 | 0.210 | 0.010 | NA | NA | NA |
| | | 3M/40° C. | 101.7 | 0.200 | 0.170 | ND | 0.030 | 0.080 | 0.520 |
| Dextrose | 0.020 | Initial | 100.9 | 0.170 | 0.310 | 0.003 | 0.090 | 0.091 | 0.574 |
| | | 1M/40° C. | 100.5 | 0.340 | 0.220 | 0.004 | 0.013 | 0.019 | 0.583 |
| | | 2M/40° C. | 100.6 | 0.280 | 0.230 | 0.010 | NA | NA | NA |
| | | 3M/40° C. | 101.0 | 0.200 | 0.190 | 0.010 | 0.030 | 0.100 | 0.570 |

TABLE V

Stability Data of an Aqueous Ready-to-Use Oxaliplatin Solutions containing Catalytic Amounts of Sucrose

| Selected Auxiliary Additives | Carbohydrate Concentration (%) | Condition | Assay (%) | Impurities (% w/w) | | | | | |
|---|---|---|---|---|---|---|---|---|---|
| | | | | A | B | C | Highest Unknown | Total Unknown | Total Impurities |
| Sucrose | 0.0010 | Initial | 99.8 | 0.190 | 0.330 | 0.002 | 0.067 | 0.067 | 0.589 |
| | | 1M/40° C. | 99.2 | 0.260 | 0.230 | 0.002 | 0.017 | 0.017 | 0.509 |
| | | 2M/40° C. | 100.1 | 0.280 | 0.250 | 0.000 | NA | NA | NA |
| | | 3M/40° C. | 99.2 | 0.200 | 0.210 | ND | 0.020 | 0.030 | 0.520 |
| Sucrose | 0.0020 | Initial | 101.3 | 0.150 | 0.330 | 0.002 | 0.061 | 0.061 | 0.543 |
| | | 1M/40° C. | 100.8 | 0.50 | 0.220 | 0.002 | 0.016 | 0.029 | 0.501 |
| | | 2M/40° C. | 101.8 | 0.260 | 0.250 | 0.000 | NA | NA | NA |
| | | 3M/40° C. | 101.8 | 0.180 | 0.210 | ND | 0.020 | 0.040 | 0.510 |
| Sucrose | 0.0025 | Initial | 100.8 | 0.210 | 0.310 | 0.002 | 0.099 | 0.114 | 0.636 |
| | | 1M/40° C. | 99.1 | 0.260 | 0.210 | 0.003 | 0.022 | 0.029 | 0.502 |
| | | 2M/40° C. | 99.8 | 0.300 | 0.200 | 0.000 | NA | NA | NA |
| | | 3M/40° C. | 98.9 | 0.210 | 0.180 | ND | 0.030 | 0.090 | 0.560 |
| Sucrose | 0.0050 | Initial | 99.0 | 0.150 | 0.340 | 0.002 | 0.060 | 0.060 | 0.552 |
| | | 1M/40° C. | 99.2 | 0.280 | 0.240 | 0.001 | 0.008 | 0.008 | 0.529 |
| | | 2M/40° C. | 99.5 | 0.270 | 0.260 | 0.000 | NA | NA | NA |
| | | 3M/40° C. | 99.8 | 0.210 | 0.200 | ND | 0.020 | 0.030 | 0.530 |
| Sucrose | 0.010 | Initial | 100.5 | 0.210 | 0.330 | 0.002 | 0.055 | 0.055 | 0.597 |
| | | 1M/40° C. | 99.7 | 0.280 | 0.260 | 0.002 | 0.011 | 0.011 | 0.533 |
| | | 2M/40° C. | 100.8 | 0.250 | 0.270 | 0.000 | NA | NA | NA |
| | | 3M/40° C. | 100.3 | 0.190 | 0.170 | ND | 0.020 | 0.030 | 0.470 |
| Sucrose | 0.020 | Initial | 102.0 | 0.200 | 0.350 | 0.002 | 0.065 | 0.065 | 0.617 |
| | | 1M/40° C. | 100.5 | 0.260 | 0.240 | 0.002 | 0.009 | 0.009 | 0.511 |
| | | 2M/40° C. | 101.7 | 0.270 | 0.280 | 0.000 | NA | NA | NA |
| | | 3M/40° C. | 100.7 | 0.190 | 0.190 | ND | 0.020 | 0.040 | 0.500 |

Clear solutions, thus obtained, can be made for human or animal consumption by conventional methods, for the treatment of a human or an animal cancerous disease, by administration of such stable pharmaceutical compositions of oxaliplatin.

We claim:

1. A storage stable pharmaceutical composition comprising:
    Oxaliplatin;
    water; and
    0.0010% to 0.05% w/v of a carbohydrate;
    the composition being a solution.

2. A pharmaceutical composition according to claim 1, wherein the composition comprises 0.0010% to 0.02% w/v carbohydrate.

3. A pharmaceutical composition according to claim 1, wherein the composition comprises 0.0010% to 0.005% w/v carbohydrate.

4. A pharmaceutical composition according to claim 1, wherein the carbohydrate is selected from lactose, dextrose, sucrose and glucose.

5. A pharmaceutical composition according to claim 1, wherein the carbohydrate is lactose.

6. A process for the preparation of a pharmaceutical composition comprising: Oxaliplatin, water, and 0.0010% to 0.05% w/v of a carbohydrate; the composition being a solution; the process comprising:
    (a) dissolving a known amount of Oxaliplatin in water;
    (b) adding an amount of carbohydrate in the range of 0.0010% to 0.05% w/v with respect to the water of step (a);
    (c) agitating the mixture of step (b) to get clear solution;
    (d) filtering the clear solution of step (c) through a filter membrane under aseptic conditions; and
    (e) filling the solution resulting from step (d) into glass vials sealed with elastomeric stoppers and aluminium flip-off seals.

7. A process for preparation of pharmaceutical composition according to claim 6, wherein the water used in step (a) is water-for-injection.

8. A process for preparation of pharmaceutical composition according to claim 6, wherein carbohydrate used in step (b) is selected from lactose, dextrose, sucrose and glucose.

9. A process for preparation of pharmaceutical composition according to claim 6, wherein the carbohydrate is lactose.

10. The storage stable pharmaceutical composition of claim 1, wherein the composition is stable at a temperature of up to 40° C. for 3 months at 75% relative humidity.

11. The storage stable pharmaceutical composition of claim 1, wherein the amount of total impurities of the composition is less than the amount of total impurities of a solution of Oxaliplatin in water comprising 5% to 50% w/v of a carbohydrate.

12. The composition of claim 1, comprising 5 mg/mL oxaliplatin.

* * * * *